(12) United States Patent
Kiefer et al.

(10) Patent No.: US 6,810,750 B1
(45) Date of Patent: Nov. 2, 2004

(54) ENCODED SURFACE ACOUSTIC WAVE BASED STRAIN SENSOR

(75) Inventors: Karl F. Kiefer, Conroe, TX (US); Kevin Champaigne, League City, TX (US); Eric Krug, The Woodlands, TX (US); Gulnara Ajupova, The Woodlands, TX (US)

(73) Assignee: Invocon, Inc., Conroe, TX (US)

( * ) Notice: Subject to any disclaimer, the term of this patent is extended or adjusted under 35 U.S.C. 154(b) by 0 days.

(21) Appl. No.: 10/393,829

(22) Filed: Mar. 20, 2003

Related U.S. Application Data

(60) Provisional application No. 60/365,726, filed on Mar. 20, 2002.

(51) Int. Cl.$^7$ .............................................. G01N 29/04
(52) U.S. Cl. ............................. 73/801; 73/587; 73/702; 73/788
(58) Field of Search ......................... 73/788, 801, 587, 73/590, 700–704

(56) References Cited

U.S. PATENT DOCUMENTS

| | | |
|---|---|---|
| 3,978,731 A | 9/1976 | Reeder et al. |
| 4,249,418 A | 2/1981 | Ebata |
| 5,821,425 A | 10/1998 | Mariani et al. |
| 6,084,503 A | 7/2000 | Ruile et al. |

*Primary Examiner*—Edward Lefkowitz
*Assistant Examiner*—Alandra Ellington
(74) *Attorney, Agent, or Firm*—Kenneth A. Roddy

(57) ABSTRACT

A passive SAW strain sensor for remotely sensing strain within a surface has a receiving SAW correlator with a signal input interdigitated transducer and a plurality of adjacent successive spaced interdigitated output transducers on a piezoelectric substrate, and a transmitting SAW correlator having a plurality of adjacent successive spaced interdigitated output transducers and a signal output interdigitated transducer on a piezoelectric substrate. The transmitting SAW correlator is affixed to or embedded in the surface such that its substrate will be stressed when the surface is strained and the receiving SAW correlator is not affixed to or embedded in the surface. The output transducers of the receiving SAW correlator and the transmitting SAW correlator are spatially placed to define a unique frequency of sensitivity, and their outputs are coupled together. A complex RF waveform signal applied to the receiving SAW correlator is transformed into an acoustic wave having a distinct output pulse that supplies power to the output transducers of the transmitting SAW correlator which is transformed into a complex RF output waveform. The application of stress on the transmitting SAW correlator shifts its center frequency proportionally and changes the frequency of the complex RF output waveform, and measurement of the center frequency change yields an indication of the applied stress.

2 Claims, 1 Drawing Sheet

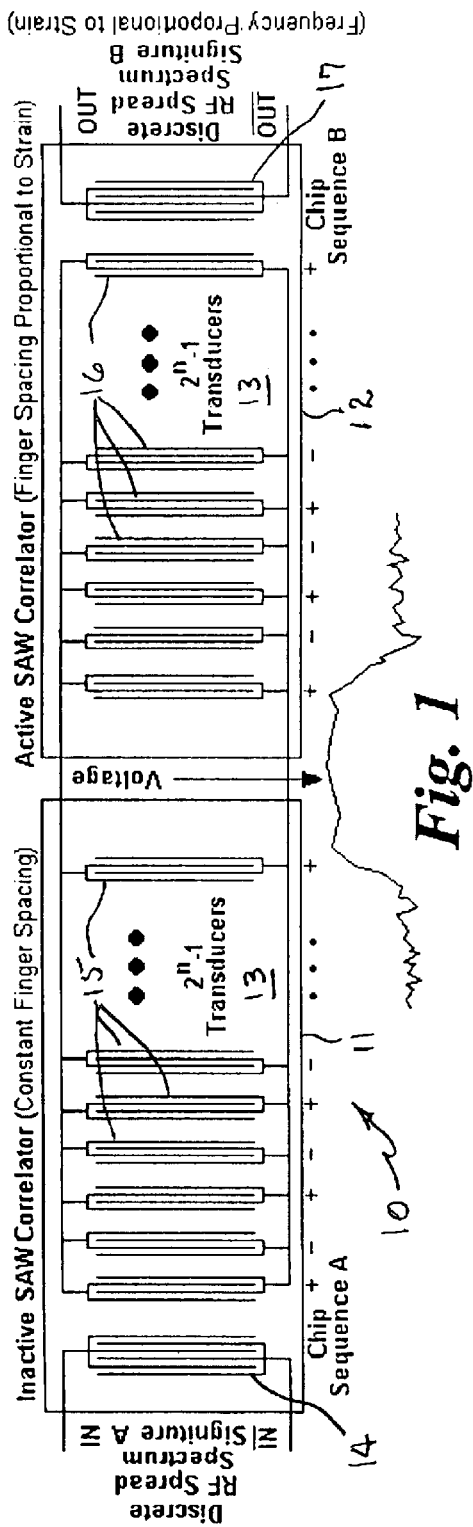
*Fig. 1*
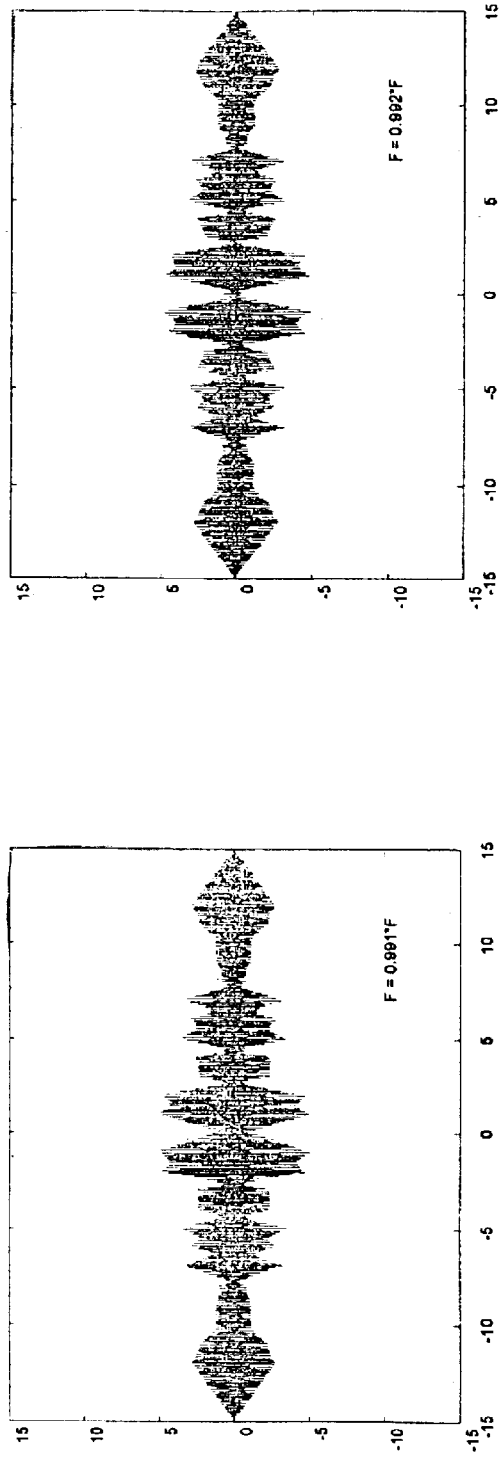
*Fig. 3*
*Fig. 2*

ENCODED SURFACE ACOUSTIC WAVE BASED STRAIN SENSOR

CROSS REFERENCE TO RELATED APPLICATION

This application claims priority of U.S. Provisional Application Ser. No. 60/365,726, filed Mar. 20, 2002.

BACKGROUND OF THE INVENTION

1. Field of the Invention

This invention relates generally to sensors that measure stresses induced on mechanical structures and surface acoustic wave (SAW) communication devices, and more particularly to a strain gauge sensor utilizing a piezoelectric "transmitting" SAW correlator affixed to or embedded into a surface and a "receiving" SAW correlator that is not affixed to the surface which receives a complex RF waveform, wherein the application of stress alters the center frequency of the "transmitting" SAW correlator, and the frequency of the complex RF output waveform and measurement of the center frequency yields an indication of the applied stress.

2. Brief Description of the Prior Art

A surface acoustic wave (SAW) filter, which is well known in the art, is typically comprised of a first set of closely-spaced, electrically conductive traces that resemble fingers (known as an interdigitated transducer), closely spaced from a second set of complimentary, interdigitated output conductive traces (known as output transducers). Both sets of fingers are etched onto the surface of a piezoelectric substrate. In SAW devices, the spacing between the interdigitated transducers affects the frequency of sensitivity.

Surface Acoustic Wave (SAW) detectors and strain gauge devices have also been proposed and implemented to some extent in the prior art; however, most of these devices have been constructed as a surface acoustic wave (SAW) filter sensitive to a particular frequency only, with no encoding.

Surface acoustic wave (SAW) transmitters having a surface acoustic wave resonator and an oscillator are also known in the art. Typically, the resonator section is comprised of a central interdigitated transducer, and a multitude of closely spaced, electrically conductive reflecting strips arranged at both sides of the interdigitated transducer. Both the interdigitated transducer and reflecting strips are deposited onto the surface of a piezoelectric substrate.

Spread Spectrum (SS) radios are well known to provide robust data transfer in varied and/or harsh radio frequency (RF). Spread spectrum (SS) radios were originally developed for military use, but are now becoming popular for commercial applications. Spread spectrum and the derivatives thereof, are quickly becoming the technology of choice for mass communications cellular based technology. Signal spreading provides significant immunity to man-made noise (intentional or unintentional) as well as a reduced probability of interference with existing equipment.

Another important benefit is that spread spectrum (SS) systems offer significant immunity to RF multipath. This is critical for transceivers located in or inside metal objects (i.e. within air frames or space frames). Multipath refers to multiple signal paths due to reflections that may exist between a transmitter and receiver. A classic example of multipath is the "ghost images", which commonly exist on a standard TV pictures. Multipath occurs when path length differences are exactly (n+½) wavelength. The resulting cancellation can be almost complete for narrow band transmissions. A spread spectrum (SS) signal, which exists over a large frequency or equivalently large wavelength range, may be partially canceled, but other portions will still be received. Since a SS signal contains significant redundancy, complete data can still be extracted from the resulting signal.

Piezoelectric materials are a unique family of materials that can be deformed by an applied electric field, and conversely, a deformation of the material produces an electric field. An antenna will reflect RF energy that is transmitted at its nominal frequency. Further, stress-induced deformation of a SAW-based sensor attached to an antenna will shift the prime frequency response causing the greatest energy to be reflected at a frequency slightly different from the nominal frequency. Therefore, an electric field imposed on the fingers causes a local deformation that launches a wave on the surface of the substrate. This surface wave can be converted back to an electrical signal by being read off another set of interdigitated transducers.

Reeder et al, U.S. Pat. No. 3,978,731 discloses a surface acoustic wave transducer wherein SAW wave are propagated across a thin, flexible diaphragm which is subjected to an applied external pressure. Since the wave velocity and path length vary with diaphragm deformation, the acoustic wave delay time is a function of the applied external pressure. Electroacoustic transducers are fabricated on opposite edges of the diaphragm for electronic excitation and detection of the surface acoustic wave. An electronic feedback path including the two transducers, the wave path, and an electronic amplifier oscillates at a frequency which is determined by the delay time required for acoustic wave propagation over the diaphragm path, and which decreases approximately linearly with applied external pressure. A second acoustic path called the reference path has a length equal to the first path and in the preferred embodiment contains a diaphragm which is subject to a different applied pressure. A second electronic feedback path composed of two transducers, the reference path and a second amplifier oscillates at a second frequency called the reference frequency. By applying a sample of the first and second oscillator voltages to a semiconductor mixer, a difference frequency output is obtained which is proportional to the differential pressure. The difference frequency output is approximately independent of temperature, and is converted to various digital codes by use of standard frequency counter circuits. If only one set of transducers is used, the device can also measure temperature in a digital manner. Stress or strain measurements may also be made by bonding the diaphragms or only the transducers directly on the physical surface to be measured.

Ebata, U.S. Pat. No. 4,249,418 discloses a temperature detector having a transmitting section including an oscillator which has a surface acoustic wave resonator that includes a Y-cut and Z-propagation piezoelectric base plate, of which the frequency characteristic varies responding to the temperature of the base plate, the oscillator generating an oscillation output of a frequency corresponding to the frequency characteristic and an antenna for transmitting the oscillation output. A receiving section includes a receiving antenna, a means for detecting the output of the receiving antenna, and a signal processing circuit for processing the output of the detecting means to generate at least one of the temperature display and control signals of the base plate of the surface acoustic wave device.

Mariani et al, U.S. Pat. No. 5,823,425 discloses a surface acoustic wave (SAW) sensing device for remotely sensing structural integrity of a physical structure. The sensing device includes a piezoelectric substrate with a notch formed part way in the bottom of the substrate and along the width thereof. The substrate is mounted to a physical structure. An antenna is coupled to the RF circuit on the substrate and is capable of receiving and transmitting a RF signal. Interdigital input and output transducers are disposed on the upper surface of the substrate. The input transducer is located adjacent one end of the substrate and the output transducer is located adjacent an opposing end of the substrate. Bus bars connect the input and output transducers. The input transducer provides a complementary first response upon receipt of an RF expanded linear/nonlinear FM signal from the antenna and transmits this compressed pulse to the output transducer. The output transducer provides a second response upon receipt of the first response and transmits the same to the antenna via the bus bar. When the substrate is strained beyond a predetermined critical level, the substrate is fractured along the notch and the first response emitted by the input transducer is prevented from being transmitted to the output transducer indicating SAW sensor failure and that structural integrity has been compromised.

Ruile et al, U.S. Pat. No. 6,084,503 discloses Radio-interrogated surface-wave technology sensor, in which the sensitive element is an impedance which is electrically connected as termination to a surface-wave structure of the sensor.

The present invention is distinguished over the prior art in general, and these patents in particular by a passive SAW strain sensor for remotely sensing strain within a surface that has a receiving SAW correlator with a signal input interdigitated transducer and a plurality of adjacent successive spaced interdigitated output transducers on a piezoelectric substrate, and a transmitting SAW correlator having a plurality of adjacent successive spaced interdigitated output transducers and a signal output interdigitated transducer on a piezoelectric substrate. The transmitting SAW correlator is affixed to or embedded in the surface such that its substrate will be stressed when the surface is strained and the receiving SAW correlator is not affixed to or embedded in the surface. The output transducers of the receiving SAW correlator and the transmitting SAW correlator are spatially placed to define a unique frequency of sensitivity, and their outputs are coupled together. A complex RF waveform signal applied to the receiving SAW correlator is transformed into an acoustic wave having a distinct output pulse that supplies power to the output transducers of the transmitting SAW correlator which is transformed into a complex RF output waveform. The application of stress on the transmitting SAW correlator shifts its center frequency proportionally and changes the frequency of the complex RF output waveform, and measurement of the center frequency change yields an indication of the applied stress.

SUMMARY OF THE INVENTION

It is therefore an object of the present invention to provide a passive SAW strain sensor for remotely sensing strain within a surface wherein the excitation signal and the readout signal will is a complex RF waveform, which will reduce noise and allow for differentiation between multiple devices in close proximity.

It is another object of this invention to provide a passive SAW strain sensor for remotely sensing strain within a surface that is extremely small does not require batteries or power-scavenging circuitry, and does not require wires or fibers to be run out from the surface being monitored.

Another object of this invention is to provide a passive SAW strain sensor for remotely sensing strain within a surface that can be interrogated from a distance using an RF signal, and a single interrogator can acquire strain data from multiple sensors.

Another object of this invention is to provide passive SAW strain sensors for remotely sensing strain within a surface that are particularly useful for non-destructive evaluation (NDE) of composite (and other) structures, which often have widely varied strength values for identical test coupons.

Another object of this invention is to provide passive SAW strain sensors for remotely sensing strain within a surface that are suited for use in non-destructive evaluation of composite materials such as composite airframes and bonding materials, and for use in inflatable bladders and airlocks, use as temperature sensors, pressure sensors, accelerometers, chemical or contamination sensors, non-contact torque sensors, automobile or aircraft non-contact tire pressure/temperature/tread measurements, implanted subcutaneous biological sensors for medical monitoring and diagnosis, and various extreme temperature range sensors.

A further object of this invention is to provide a passive SAW strain sensor for remotely sensing strain within a surface that utilizes Direct Sequence Spread Spectrum (DSSS) transmission technology which allows spectral reuse by utilizing different chipping sequences for different communication channels whereby multiple sets of sensors can be simultaneously communicating using the same band of frequencies.

A still further object of this invention is to provide a passive SAW strain sensor for remotely sensing strain within a surface that is simple in construction, inexpensive to manufacture, and rugged and reliable in operation.

Other objects of the invention will become apparent from time to time throughout the specification and claims as hereinafter related.

The above noted objects and other objects of the invention are accomplished by a passive SAW strain sensor for remotely sensing strain within a surface that has a receiving SAW correlator with a signal input interdigitated transducer and a plurality of adjacent successive spaced interdigitated output transducers on a piezoelectric substrate, and a transmitting SAW correlator having a plurality of adjacent successive spaced interdigitated output transducers and a signal output interdigitated transducer on a piezoelectric substrate. The transmitting SAW correlator is affixed to or embedded in the surface such that its substrate will be stressed when the surface is strained and the receiving SAW correlator is not affixed to or embedded in the surface. The output transducers of the receiving SAW correlator and the transmitting SAW correlator are spatially placed to define a unique frequency of sensitivity, and their outputs are coupled together. A complex RF waveform signal applied to the receiving SAW correlator is transformed into an acoustic wave having a distinct output pulse that supplies power to the output transducers of the transmitting SAW correlator which is transformed into a complex RF output waveform. The application of stress on the transmitting SAW correlator shifts its center frequency proportionally and changes the frequency of the complex RF output waveform, and measurement of the center frequency change yields an indication of the applied stress.

BRIEF DESCRIPTION OF THE DRAWINGS

FIG. 1 is a schematic diagram of a strain gauge sensor utilizing two fixed sequence surface acoustic wave (SAW) correlators in accordance with the present invention.

FIG. 2 is a graph showing expected correlation values vs. relative chip time for a Frequency Delta of $0.991*F_0$.

FIG. 3 is a graph showing expected correlation values vs. relative chip time for a Frequency Delta of $0.992*F_0$.

DESCRIPTION OF THE PREFERRED EMBODIMENTS

Referring to the drawings by numerals of reference, there is shown in FIG. 1, a schematic diagram of a strain sensor 10 utilizing two fixed sequence surface acoustic wave (SAW) correlators 11 and 21, each having a set of finger-like electrically conductive interdigitated transducers etched onto the surface of a piezoelectric substrate 13, such as quartz, lithium niobate, or gallium arsenide (GaAs). The correlators form a passive matched filter for symbol detection and symbol generation.

The surface acoustic wave (SAW) correlator 11, on the left-hand side of the figure, hereinafter referred to as the "receiving" SAW correlator has a signal input interdigitated transducer 14 on the left-hand side and a series of successive signal sampling interdigitated output transducers 15 extending to the right, which are spatially placed for a temporal delay of one chip period. The input interdigitated transducer 14 of the "receiving SAW correlator 11 is adapted to be connected with an antenna (not shown) to receive a complex waveform RF input signal from an interrogating device (not shown).

The surface acoustic wave (SAW) correlator 12, on the right-hand side of the figure, hereinafter referred to as the "transmitting" SAW correlator has a series of successive signal sampling interdigitated output transducers 16 extending to the right, which are spatially placed for a temporal delay of one chip period, and a signal output interdigitated transducer 17 on the right-hand side.

The outputs of the output transducers 15 and 16 of the "receiving SAW correlator 11 and the "transmitting" SAW correlator 12 are coupled together. The "transmitting" SAW correlator 12 is affixed to or embedded into the surface of a composite or other structure, such as a carbon fiber laminate or other material, while the "receiving" SAW correlator 11 is not. Thus, the "receiving" SAW correlator 11 is inactive and is not affected by strain, while the "transmitting" SAW correlator 12 is active and becomes slightly stretched and compressed by strain.

The input interdigitated transducer 14 of the "receiving" SAW correlator 11 is connected with an antenna to receive a RF input signal from an interrogating device (not shown), hereinafter referred to as the "system interrogator". When an input signal is launched on the input interdigitated transducer 14 of the "receiving" SAW correlator 11, the signal then propagates to the right and is sampled by the successive output transducers 15. The polarity of connection (phase) of the output transducers 15 is matched to a desired symbol or chipping sequence. When a signal is applied to the "receiving" SAW correlator, which exactly matches the hardwired chipping sequence, an output correlation pulse occurs at a baseband data rate. This pulse then supplies the power to the output transducers 16 of the "transmitting" SAW correlator 12 that works in reverse. The voltage generates a mechanical wave on the "transmitting" SAW correlator 12 according to the hardwired finger pairs. This then propagates to the right and is again output by the output interdigitated transducer 17 as a complex RF signal.

Since the spacing between the interdigitated transducers affects the frequency of sensitivity, the application of stress alters the spacing between the fingers of the output transducers 16 of the "transmitting" SAW correlator 12 when it becomes slightly stretched and compressed by strain, and the center frequency shifts proportionally. This action on the active SAW will change the frequency of the complex RF output waveform. Measurement of the center frequency change will yield an indication of the applied stress.

In the above example, and as illustrated in FIG. 1, the system interrogator will transmit a complex waveform "A" that will create a correlation for the surface acoustic waves (SAWs) with the appropriate Chip Sequence "A". The interrogator will then look for a received complex RF message with signature "B" and will note its frequency. Additionally, the use of slightly different center frequencies on multiple devices operating simultaneously is possible. Simulation and actual test results have shown that frequency shifts as small as 1% in the center frequency are sufficient to give no signal response, despite the fact that the bandwidth of the device is very large (>150 MHz, for example).

Because a complex RF waveform is transmitted and then read out, rather than a single frequency, interference from other similar sensors, as well as other RF transmitters in the same frequency band is significantly reduced. Thus, literally hundreds of gauges may be placed within one RF space without mutual interference, and multiple sensors can be addressed using unique code identifiers. The embedded SAW strain gauge can be designed with a specific sequence encoded into the correlators so that one SAW could be differentiated from another. In this way, a single interrogator can acquire strain data from multiple sensors.

In operation, the system interrogator sweeps the frequencies that it used to interrogate the sensor, and then determines the center frequency by recording the highest amplitude return transmission. If the frequency delta between the system interrogator and the sensor is large enough to cause a drop in the correlation value, but not large enough to lose correlation, two correlation peaks are observed, one on each side of the center as shown in the graph of FIG. 2. FIG. 2 shows expected correlation values vs. relative chip time for a Frequency Delta of $0.991*F_0$.

As the frequency delta becomes smaller, the separation between the two center peaks changes, as shown in FIG. 3. FIG. 3 shows expected correlation values vs. relative chip time for a Frequency Delta of $0.992*F_0$.

Thus if the system interrogator measures the time between the dual correlation peaks, an accurate measurement of the strain experienced by sensor can be made. This technique may or may not yield more accurate results for static measurements, but since the measurement can be made by sending just a single code, the sample rates can be extremely fast, potentially in the multiple megahertz range or faster, depending upon the recovery time of the time to digital conversion (TDC) circuitry. Fine measurements on the returned waveform allows for resolution similar to a standard strain gauge. The temperature effects can be measured and subtracted from the strain measurement.

The system interrogators are mounted on the outside of the structure at some distance from the sensor elements, and the sensor elements can be interrogated from a distance using an RF signal, which provides a significant advantage over a conventional resistive strain gauge. The acceptable distance between the sensor and the interrogator is dependent upon the RF energy transmitted, the RF coupling between the transmitter and the sensor, and the attenuation of the RF energy along the transmission path.

The present sensors utilize Direct Sequence Spread Spectrum (DSSS) technology wherein the spreading sequence or chip rate, which is usually at least an order-of-magnitude greater than the actual data rate. DSSS signals also offer the advantage of allowing for spectral reuse by using different chipping sequences for different communication channels in the same frequency band. Thus, multiple sets of transceivers can be simultaneously communicating using the same band of frequencies, known as Code Division Multiple Access (CDMA).

The present surface acoustic wave (SAW) correlators can be extremely small (<2 mm$^3$), and require no internal power source, and require no wires or fibers to be run within or out from internal layers of the surface being monitored. They perform the primary function of a digital signal processor similar to a conventional DSSS receiver, but with no power consumption.

The present SAW correlator sensors are particularly useful for non-destructive evaluation (NDE) of composite (and other) structures. The ability to embed a 2 mm$^3$ sensor with no wires in a composite material versus a wired or optical strain gauge is significant, since composite materials are not as well understood as metals, and often strength values vary widely for identical test coupons.

Other applications include non-destructive evaluation of composite materials as used in composite airframes and bonding materials. Additionally, stress can be remotely monitored within any non-metallic material, such as inflatable bladders and airlocks. If isolated from a structure, the thermal expansion coefficient of the present SAW correlator sensors can be used to produce a temperature sensor. The present SAW strain gauges can also be used as a pressure sensor with the addition of a diaphragm structure, or as an accelerometer with the addition of a proof mass structure. All sensor techniques that traditionally utilize a SAW filter would be viable candidates as well, such as chemical sensors or contamination sensors. Extreme temperature sensors, from cryogenics to greater than 600° C., may also be possible. Only packaging materials and techniques would limit the temperature range, since the piezoelectric nature of materials is generally not affected by temperature (only the melting point of the piezoelectric would be a limitation).

Still other commercial applications of the technology include non-contact torque sensors, automobile or aircraft non-contact tire pressure/temperature/tread measurements, implanted subcutaneous biological sensors for medical monitoring and diagnosis, and various extreme temperature range sensors.

While this invention has been described fully and completely with special emphasis upon a preferred embodiment, it should be understood that within the scope of the appended claims the invention may be practiced otherwise than as specifically described herein.

What is claimed is:

1. A passive SAW strain sensor for remotely sensing strain within a surface, comprising:
    a receiving SAW correlator having a signal input interdigitated transducer and a plurality of adjacent successive spaced interdigitated output transducers on a piezoelectric substrate, said receiving SAW correlator not affixed to or embedded in the surface so as to be unaffected by strain when the surface is strained; and
    a transmitting SAW correlator having a plurality of adjacent successive spaced interdigitated output transducers and a signal output interdigitated transducer on a piezoelectric substrate, said transmitting SAW correlator affixed to or embedded in the surface such that its said substrate will be stressed when the surface is strained;
    said interdigitated output transducers of said receiving SAW correlator and said transmitting SAW correlator spatially placed to define a unique frequency of sensitivity, and outputs of said interdigitated output transducers of said receiving SAW correlator and said transmitting SAW correlator being coupled together; wherein
    a complex RF waveform signal applied to the receiving SAW correlator which exactly matches the frequency of sensitivity is transformed into an acoustic wave having a distinct output pulse that supplies power to said output transducers of said transmitting SAW correlator which is transformed into a complex RF output waveform; and
    the application of stress on said transmitting SAW correlator shifts its center frequency proportionally and changes the frequency of the complex RF output waveform, and measurement of the center frequency change yields an indication of the applied stress.

2. A method of remotely sensing strain within a surface utilizing a passive surface acoustic wave, comprising the steps of:
    providing a receiving SAW correlator having a signal input interdigitated transducer and a plurality of adjacent successive spaced interdigitated output transducers on a piezoelectric substrate, and a transmitting SAW correlator having a plurality of adjacent successive spaced interdigitated output transducers and a signal output interdigitated transducer on a piezoelectric substrate, said interdigitated output transducers of said receiving SAW correlator and said transmitting SAW correlator spatially placed to define a unique frequency of sensitivity, and outputs of said interdigitated output transducers of said receiving SAW correlator and said transmitting SAW correlator being coupled together;
    affixing or embedding only said transmitting SAW correlator onto or in the surface such that its said substrate will be stressed when the surface is strained;
    transmitting a RF signal to said input transducer means;
    transmitting a complex RF waveform signal to said input interdigitated transducer of said receiving SAW correlator and transforming it into an acoustic wave having a distinct output pulse that supplies power to said output transducers of said transmitting SAW correlator which is then transformed into a complex RF output waveform;
    allowing said transmitting SAW correlator to shift its center frequency proportionally the application of stress on its said substrate and thereby change the frequency of the complex RF output waveform; and
    measuring the center frequency change to yield an indication of the applied stress.

* * * * *